United States Patent [19]

Cointment

[11] 4,332,408

[45] Jun. 1, 1982

[54] DEVICE FOR REMOVING AND REPLACING SOFT CONTACT LENSES WORN ON THE HUMAN EYE

[76] Inventor: Delma M. Cointment, 914 Pontalba St., New Orleans, La. 70124

[21] Appl. No.: 179,409

[22] Filed: Aug. 18, 1980

Related U.S. Application Data

[60] Division of Ser. No. 950,555, Oct. 12, 1978, Pat. No. 4,238,134, which is a continuation of Ser. No. 773,473, Mar. 2, 1977, abandoned.

[51] Int. Cl.³ .............................................. A61F 9/00
[52] U.S. Cl. ................................................. 294/1 CA
[58] Field of Search ................. 294/1 CA, 1 R, 64 R; 128/300, 303 R; 206/5.1; 248/362, 363; 351/160

[56] References Cited

U.S. PATENT DOCUMENTS

| 4,026,591 | 5/1977 | Cleaveland | 291/1 CA |
| 4,071,272 | 1/1978 | Drdlik | 291/1 CA |

Primary Examiner—James B. Marbert
Attorney, Agent, or Firm—James A. Wong

[57] ABSTRACT

Squeezed, the flexible cup of the device forms two convex lips which grip a soft contact lens in place on a human eye, deforms the lens, breaking its fluid suction-bond to the eye, allowing easy and gentle removal of the lens from the eye, without fingers touching the eye. The body of the device has a dished end with an elevated rim, an annular lumen and a depressed central segment, which end safely holds soft contact lenses by the variable suction of a flexible bulb, controllable by sliding the other end of the body into the lumen of the bulb. The lens is released by squeezing the bulb.

5 Claims, 5 Drawing Figures

DEVICE FOR REMOVING AND REPLACING SOFT CONTACT LENSES WORN ON THE HUMAN EYE

This is a division of my copending application Ser. No. 950,555, filed Oct. 12, 1978, now U.S. Pat. No. 4,238,134 which in turn is a continuation of my then copending application Ser. No. 773,473, filed Mar. 2, 1977, and now abandoned.

This invention is a device for the removal, handling and replacement of soft contact lenses worn on the cornea of the human eye. It consists of a flexible cup, a body and a bulb. The flexible cup is used for the removal of a soft contact lens from the eye. Squeezed by the fingers, the cup forms two convex lips which grip and gently deform the lens, breaking its fluid suction-bond to the cornea and holding the lens for removal. One end of the body of the device is designed to hold soft contact lenses without significant deformation, for handling and for replacing the lens on the eye. A flexible bulb at the other end of the body slides along the body for varying the volume of the lumen of the bulb, to vary the suction for holding the lens and pressure for releasing it. The fingers do not touch the eye during use of the device.

In the current state of the art, contact lenses are worn over the cornea of the human eye for the correction of visual defects. The lenses are of two types, hard and soft and both are held to the cornea by a fluid suction-bond. The hard lenses afford correction by the difference in curvature of their inner and outer surfaces. The fluid suction-bond of the soft lens to the eye shapes the inner curvature of the soft lens to the curvature of the cornea, so the correction these lenses afford is due to the difference in curvature of the cornea of the eye and the curvature of the outer surface of the soft lens. Hard contact lenses are of diameters usually less than the diameter of the cornea they cover, while soft contact lenses are usually larger in diameter than the cornea, or almost as large as the cornea. When a hard lens is to be removed from the eye, it is moved off of the cornea, on to the sclera, by a finger or by a suction cup device, to a point where the curvature of the eye is different from the fixed curvature of the undersurface of the hard lens. The difference in curvature breaks the fluid suction-bond of the hard lens to the eye, allowing easy removal of the lens. A soft lens moved off of the cornea by a finger or by a suction cup, does not respond as does the hard lens. The soft contact lens, so moved, merely alters its shape and continues to conform to the external surface of the eye. The fluid suction-bond of the soft lens to the eye does not break and the lens cannot be removed from the eye without considerable pushing, manipulation and pulling. Pushing on the eye is very undesirable and when a soft lens on the eye is pulled, the fluid suction-bond of the lens to the eye holds and the eye itself is pulled out of shape, which is capable of causing injury to the eye.

Devices used to grip or hold hard contact lenses are either simple suction cups or else they are cups which apply suction to the lens through a single hole in the cup. These devices are completely unsatisfactory for handling soft contact lenses. They do not break the fluid suction-bond of the soft lens to the eye and pulling on them transmits the pull through the soft lens to pulling of the eye itself. The plain suction cups do not release soft contact lenses when the lenses are positioned on the eye and those devices which apply suction through a single hole do not hold soft lenses at all well and distort the lenses at the point of suction to where the lenses can be damaged.

Currently, those who wear soft contact lenses remove the lenses from their eyes with their fingers. The lenses are wet, smooth and slippery. Fingers do not grip the lenses at all well or with sufficient friction to break the fluid suction-bond of the lens to the eye without undesirable pressure on the eye itself. The fingers also frequently touch and abrade the surface of the eye, injuring the cornea and/or the sclera and can also damage the soft lens.

What is new in this application is that the convex lips which the flexible lens removal cup of this invention forms when squeezed, readily grips the outer surface of a soft contact lens which is in place on the eye, gently changes the curvature of the lens by deformation, which breaks the fluid suction-bond of the soft lens to the eye without significant pressure on the eye, so the lens is easily and gently removed from the eye.

Also new in this application is the design of the dished end of the body of the device, which holds a soft contact lens by suction over a circular, annular area and which has a depressed, central segment, which, combined, prevents significant deformation of a lens by the suction applied. The suction which holds the lens derives from a flexible suction bulb. The body of the device can be moved into the lumen of the suction bulb to alter its suction/pressure characteristics. When squeezed, the bulb supplies the pressure needed to release the lens.

Figure 1:
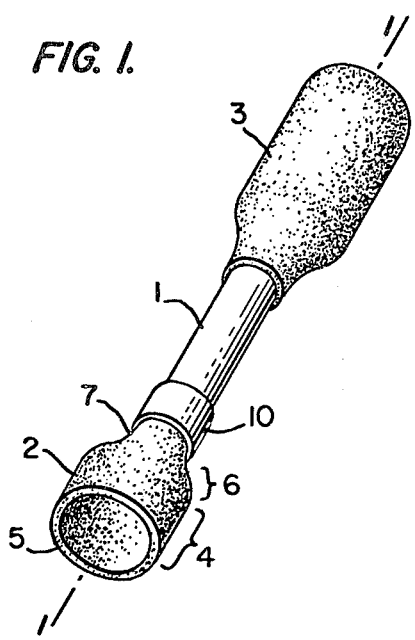
FIG. 1 is a perspective view of the device with the lens removing cup on one end of the body and the suction bulb on the other.
Figure 2:
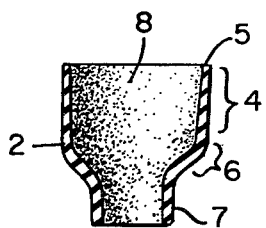
FIG. 2 is a cross sectional view of the lens removing cup, along line 1—1 of FIG. 1.

The device is pictured in FIG. 1 and consists of a body, 1, with the lens removal cup, 2, on one end and a suction bulb, 3, on the other. The body 1, is made of hard or semi-hard plastic or other suitable material. The lens removal cup 2, is of soft, flexible plastic, silicone rubber, or other suitable material and the suction bulb 3, is of soft flexible plastic, rubber or other suitable material. As shown in FIGS. 1 and 2, the flexible lens removing cup 2 has a hollow, tubular body, 4, which is of a diameter approximating that of soft contact lenses. The outer edge of body 4 of cup 2, forms rim 5. The other end of body 4 of cup 2 reduces in diameter, at 6, to form a short, tubular end, 7, which is of smaller diameter than body 4. The inside of small end 7 fits over end 11 of body 1 of the device and is of such size that cup 2 can be easily placed on and removed from end 11 of body 1. The cup 2 is completely hollow, its lumen 8 being open at both ends. The various segments of cup 2 are generally proportioned as shown in FIGS. 1 and 2 and 3 and experimentation has established the approximate proportions shown are the most effective.

Figure 3:
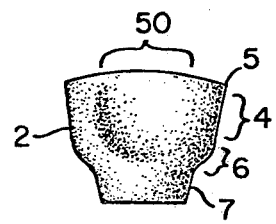
FIG. 3 is a view of the lens removing cup showing the convex lips which form when the cup is squeezed.

The shape and relative proportions of the various segments of cup 2 is a fundamental part of this invention, for when body 4 and reduction segment 6 of cup 2 of this device is squeezed, outer rim 5 of the cup 2 flattens, forming two lips which curve convexly outward as shown at 50 of FIG. 3. It is this convexity 50 of the lips which rim 5 of lens holding cup 2 forms when cup 2 is squeezed, which enable cup 2 to effectively grip a soft contact lens over the cornea of an eye, deform the lens, breaking its fluid suction-bond to the eye and hold the lens, so it is easily removed from the eye. When a plain, cylindrical tube is squeezed, its free rim forms lips which are concave. They curve inward, toward the body of the tube and do not grip a soft contact lens at all well. Neither convex lips, molded or formed on the end of a plain, cylindrical tube or convex lips molded onto a spring device grip a soft contact lens as effectively as the cup, 2, of this device, of this application.

Figure 4:
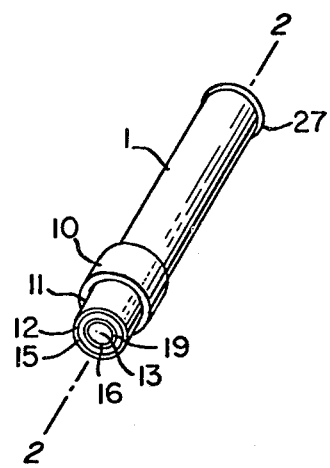
FIG. 4 is a perspective view of the body of the device.

Body 1 of the device, as shown in FIG. 4 has end 11, over which small end 7 of lens removal cup 2, fits. Shoulder 10, on body 1, forms a stop for end 7 of lens removal cup 2, so end 11 of body 1 will not protrude too far into lumen 8 of the lens removal cup 2, i.e., not further into lumen 8 of cup 2, than the beginning of reduction segment 6. Face 12, of end 11, of body 1, is concave, with elevated, rounded rim 15. In the center of this face 12 is a removable plug, 16. Face 13, of plug 16, is also concave, with concavity matching the concavity of face 12, face 13 of plug 16 setting very slightly below the projected concavity of face 12. Body 1 of the device has an axial hole through its center, forming lumen 18. At end 11 of body 1, lumen 18 is enlarged, forming step 28 and lumen 19. Plug 16, which is removable, is of hard plastic, semi-hard plastic, metal, or other suitable material. The body of plug 16 fits in lumen 19 and is slightly smaller in diameter than lumen 19, giving lumen 19 an annular shape. The base of plug 16 seats against step 28 of lumens 18 and 19 of body 1 and stem 17, of plug 16, fits snugly into lumen 18 of body 1, holding plug 16 in place. Stem 17 has a longitudinal hole axially through its center, forming lumen 20, which communicates with lumen 21 of a cross hole through the base of the body of plug 16, so lumen 18 of body 1 communicates with annular lumen 19 of the dish shaped end of body 1, through lumens 20 and 21 of plug 16.

All surfaces of the device which may contact a soft contact lens are smooth and all edges which may contact a lens are smoothly rounded. Plug 16 can be easily removed for cleaning of the device, by pushing it out of the body with a stylus of suitable size, passing through lumen 18 of body 1. Plug 16 is easily reinserted by simply pushing it back into place.

Figure 5:
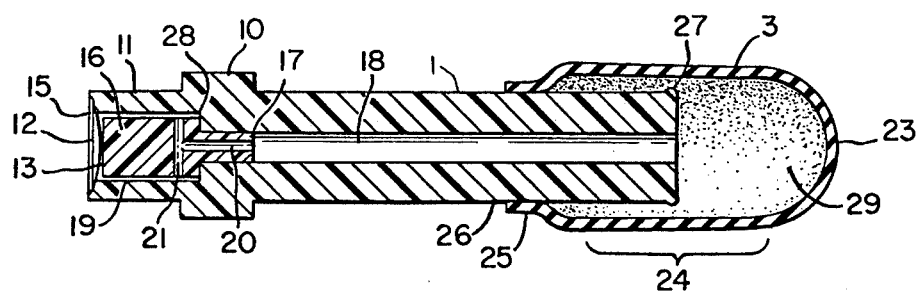
FIG. 5 is an enlarged, cross sectional view of the body and the suction bulb of the device, along line 1—1 of FIG. 1, and line 2—2 of FIG. 4.

Suction bulb 3, shown in cross section in FIG. 5, is of the general shape of a prolate spheroid, with rounded end 23, cylindrical body 24, reduced to form rim 25, which is a smooth, sliding fit over end 26 of body 1. Rim 27 is at end 26 of body 1, to prevent inadvertent sliding off of bulb 3. Sliding end 26 of body 1 into lumen 29 of suction bulb 3 diminishes the volume of lumen 29, for limitation and for variance of the suction characteristics of bulb 3. The lens is held by suction applied to it over a broad area by an annular lumen in the dished end of the device and the depressed central segment of the dish supports the lens, preventing undue distortion thereof. Pressure on the flexible bulb releases the lens.

What is claimed is:

1. A device for handling and inserting soft contact lenses comprising in combination:
   a. a tubular body member formed with a lumen or axial hole extending from a first end to a second end thereof;
   b. a suction bulb of flexible material with an opening through which said tubular body member extends adjacent said first end of said tubular body member; and
   c. a plug disposed within said tubular body member adjacent said second end of said tubular body member;
   wherein said lumen is formed with an enlarged portion adjacent said second end of said tubular body member; said plug includes a main body portion and a stem portion with said main body portion being slightly smaller in diameter than and extending substantially coaxially within said enlarged portion, thus forming an annular passage therebetween; said stem portion extends axially inwardly beyond said enlarged portion of said lumen and is in snug contact with a smaller diameter, axially inward part of said lumen; and said plug is formed with an axial passage in said stem portion and a diametrically extending passage in said main body portion intersected by said axial passage whereby fluid communication is established between the interior of said suction bulb and said lumen at said section end by way of said lumen at said first end, said axial passage, said diametrically extending passage, and said annular passage.

2. The device for handling and inserting soft contact lenses as defined in claim 1, wherein said suction bulb includes an axially extending rim providing a sliding fit with said tubular body member and said tubular body member includes a radially outwardly extending rib adjacent said first end to preclude said suction bulb from sliding off said tubular body member.

3. The device for handling and inserting soft contact lenses as defined in claim 1 or claim 2, wherein said tubular body member is formed with a concave face at said second end having a concavity compatible with that of soft contact lens to be handled thereby and wherein said plug also is formed with a concave face with a concavity matching that of said concave face of said tubular body member.

4. The device for handling and inserting soft contact lenses as defined in claim 3 which is adaptable to receiving lens removing cup over said second end of said tubular body member, including a circumferentially extending shoulder adjacent to but axially inwardly from said second end whereby axial penetration of a lens removing cup by said tubular body member is limited.

5. The device for handling and inserting soft contact lenses as defined in claim 4, wherein said tubular body member is made of a hard or semi-hard plastic material.

* * * * *